US012758780B2

(12) United States Patent
Kang et al.

(10) Patent No.: US 12,758,780 B2
(45) Date of Patent: Oct. 13, 2026

(54) SEQUENTIAL LOCAL ELECTRICAL STIMULATION DEVICE AND METHOD

(71) Applicant: POSTECH Research and Business Development Foundation, Pohang-si (KR)

(72) Inventors: Won Ok Kang, Pohang-si (KR); Sung Min Park, Pohang-si (KR)

(73) Assignee: POSTECH RESEARCH AND BUSINESS DEVELOPMENT FOUNDATION, Pohang-si (KR)

( * ) Notice: Subject to any disclaimer, the term of this patent is extended or adjusted under 35 U.S.C. 154(b) by 248 days.

(21) Appl. No.: 18/510,528

(22) Filed: Nov. 15, 2023

(65) Prior Publication Data

US 2025/0001182 A1 Jan. 2, 2025

(30) Foreign Application Priority Data

Nov. 16, 2022 (KR) ........................ 10-2022-0153317
Jun. 29, 2023 (KR) ........................ 10-2023-0084372
Oct. 31, 2023 (KR) ........................ 10-2023-0147949

(51) Int. Cl.
*A61N 1/36* (2006.01)
*A61N 1/05* (2006.01)

(52) U.S. Cl.
CPC ........... *A61N 1/36185* (2013.01); *A61N 1/05* (2013.01); *A61N 1/36175* (2013.01); *A61N 1/36178* (2013.01)

(58) Field of Classification Search
CPC .. A61N 1/36185; A61N 1/05; A61N 1/36175; A61N 1/36178; A61N 1/36; A61N 1/36064; A61N 1/0534; A61N 1/36146
See application file for complete search history.

(56) References Cited

U.S. PATENT DOCUMENTS 9,760,688 B2 * 9/2017 McIntyre ........... A61N 1/36146
2013/0218232 A1 8/2013 Giftakis et al.
2022/0110694 A1 4/2022 Williams et al.

FOREIGN PATENT DOCUMENTS

JP 2019-519297 A 7/2019
KR 10-2022-0121035 A 8/2022

OTHER PUBLICATIONS

Office Action in Korean Publication No. 10-2023-0147949, dated Sep. 19, 2025, 5 pages.
Notice of Allowance in Korean Application No. 10-2023-0084372, dated Dec. 19, 2025. 1 (Note: KR1020220121035 and U.S. Pat. No. 20130218232 are of record, and the Sung-Min Park article is not prior art).

* cited by examiner

*Primary Examiner* — Paula J Stice
(74) *Attorney, Agent, or Firm* — Morgan, Lewis & Bockius LLP

(57) ABSTRACT

The present disclosure relates to a sequential local electrical stimulation method. The sequential local electrical stimulation method according to the present disclosure includes determining a number and arrangement of electrodes included in an electrode array according to a structure of a target area, determining stimulation parameters including stimulation intensity, a stimulation sequence, and a stimulation pulse based on the structure of the target area, and sequentially applying stimulation in one direction from an outermost part of the electrode array by using the stimulation parameters.

19 Claims, 24 Drawing Sheets

SEQUENTIAL LOCAL ELECTRICAL STIMULATION DEVICE AND METHOD

CROSS-REFERENCE TO RELATED APPLICATIONS

This application is based on and claims the benefit of and priority to Korean Patent Application No. 10-2022-0153317, filed on Nov. 16, 2022, Korean Patent Application No. 10-2023-0084372, filed on Jun. 29, 2023, and Korean Patent Application No. 10-2023-0147949, filed on Oct. 31, 2023, in the Korean Intellectual Property Office, the entirety of each of which is incorporated herein by reference for all purposes.

BACKGROUND

The present disclosure relates to a sequential local electrical stimulation device and sequential local electrical stimulation method, and particularly, to a sequential local electrical stimulation device that provide sequential narrow-field (SNF) stimulation capable of effectively improving symptoms in a short period of time while minimizing an impact of electric field scattering on areas surrounding a target area and a sequential local electrical stimulation method of the sequential local electrical stimulation device.

An electrical stimulation therapy is being used to treat and relieve symptoms of various diseases caused by damage to a central nervous system.

For example, epilepsy is one of the most common neurological disorders, affecting nearly 70 million people worldwide. Epileptic seizures are caused by abnormally excessive or simultaneous electrophysiological activity of the brain. Therefore, the known treatment, such as anticonvulsants (ASMs) or ablative surgery, has been used for decades to suppress or eliminate neural circuit dysfunction. Despite optimal treatment using ASM, approximately 30% of patients are known to be drug refractory. Surgical resection of the epileptogenic area may be an effective treatment option for single paroxysmal attacks but is not suitable for critical areas or multiple epileptogenic areas. Recently, deep brain stimulation (DBS), which controls epileptic circuits in a spatial and temporal manner, has been introduced as an alternative and less invasive treatment method for intractable epilepsy compared to surgical approach. Several brain areas, such as hippocampus, anterior nucleus of the thalamus (ANT), central thalamic nucleus (CM), and motor cortex, have been identified as appropriate sites for delivering stimulation therapy, but optimal target selection and stimulation parameters remain as the subject of extensive debate.

The hippocampus has been regarded as a promising stimulation target in epilepsy due to intrinsic anatomical connectivity related to generation and propagation of epileptic seizures in temporal lobe epilepsy (TLE) that is the most prevalent type of epilepsy. Numerous studies have been conducted to investigate stimulation parameters of hippocampal stimulation and therapeutic efficacy, and the study results support a possibility of hippocampal stimulation as a therapeutic method for improving epilepsy. An in vivo study comparing antiseizure effects during unilateral versus bilateral hippocampal DBS in a rat model of TLE suggested that targeting larger areas of the hippocampus may provide higher antiseizure efficacy. Also, several clinical reviews of DBS targeting techniques have suggested that the relatively large structures of the hippocampus may have an advantage in determining electrode configuration compared to other deep brain tissues having smaller volumes, such as ANT and CM. Also, because the seizure initiation zone of TLE is typically located in the hippocampus, direct adjustment targeting formation of the hippocampal may immediately terminate or suppress the epileptiform network, which means that early termination of seizures of TLE may be theoretically possible by using hippocampal stimulation. Although these scientific findings support clinical benefits of hippocampal stimulation for the treatment of epilepsy, the clinical application of hippocampal stimulation is still in an infancy stage, and several challenges are involved to develop essential DBS treatment-related knowledge, such as spatial characteristics of stimulation targets and connected networks and optimal stimulation parameters.

Also, stimulation applied extensively to the large, oval-shaped hippocampal structure by using the known DBS method called WF stimulation may cause inappropriate or excessive effects on adjacent structures, such as the amygdala, entorhinal cortex, and parahippocampal gyrus, resulting in a variety of side effects, such as memory and mood disorders.

SUMMARY

The present disclosure provides a sequential local electrical stimulation device that provides sequential narrow-field (SNF) stimulation capable of effectively improve symptoms in a short period of time while minimizing an impact on surrounding areas of a target area and a sequential local electrical stimulation method of the sequential local electrical stimulation device.

According to an aspect of the present disclosure, a sequential local electrical stimulation device includes an electrode array including multiple electrodes wherein a number and arrangement of the multiple electrodes are determined according to a structure of a target area, a stimulation generator configured to apply electrical stimulation to the target area through the electrode array, and a stimulation controller configured to determine stimulation parameters including stimulation intensity, a stimulation sequence, and a stimulation interval based on the structure of the target area and configured to control the stimulation generator according to the determined stimulation parameters.

According to another aspect of the present disclosure, a sequential local electrical stimulation method using a sequential local electrical stimulation device includes determining a number and arrangement of electrodes included in an electrode array according to a structure of a target area, determining stimulation parameters including stimulation intensity, a stimulation sequence, and a stimulation pulse based on the structure of the target area, and sequentially applying stimulation in one direction from an outermost part of the electrode array by using the stimulation parameters.

BRIEF DESCRIPTION OF THE DRAWINGS

Embodiments of the inventive concept will be more clearly understood from the following detailed description taken in conjunction with the accompanying drawings in which.

DETAILED DESCRIPTION OF THE EMBODIMENTS

Figure 1:
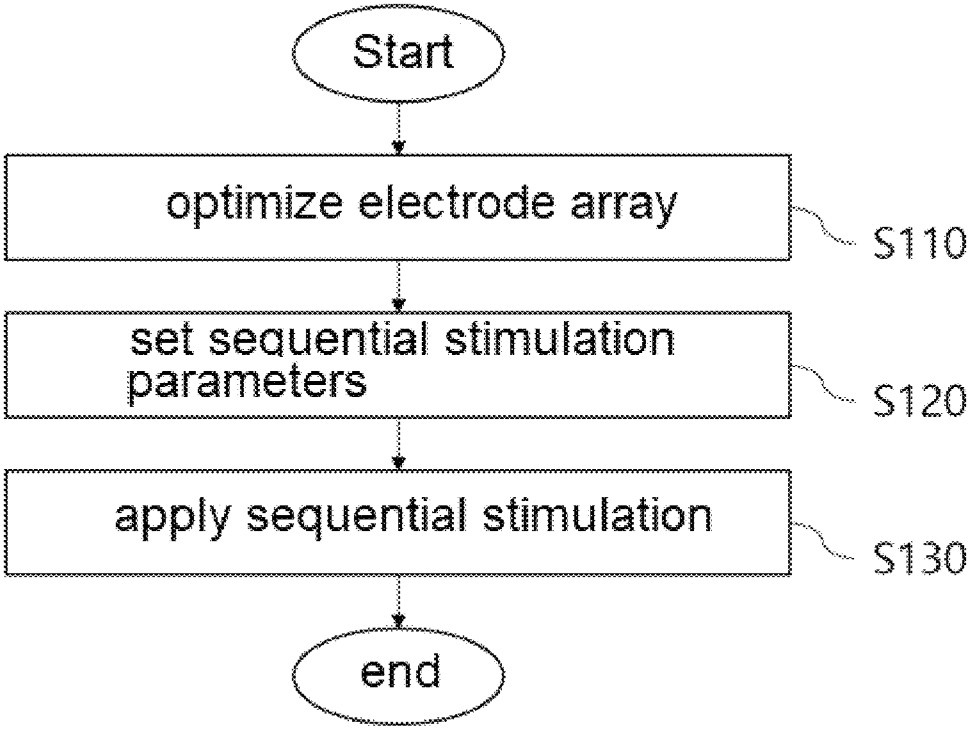
FIG. 1 is a flowchart illustrating a sequential local electrical stimulation method according to an embodiment of the present disclosure.

Hereinafter, preferred embodiments according to the present disclosure are described in detail with reference to the attached drawings. In this process, thicknesses of lines or sizes of components illustrated in the drawings may be exaggerated for the sake of clarity and convenience of description.

Also, the terms described below are defined in consideration of functions of the present disclosure and may change depending on the intention or custom of a user or operator. Therefore, definitions of the terms should be made based on descriptions throughout the present disclosure.

FIG. 1 is a flowchart illustrating a sequential local electrical stimulation method according to an embodiment of the present disclosure.

As illustrated in FIG. 1, the sequential local electrical stimulation method according to the embodiment of the present disclosure may include step S110 of optimizing an electrode array, step S120 of setting a sequential stimulation parameter, and step S110 of applying a sequential stimulation.

In step S110 of optimizing an electrode array, the electrode array may be optimized by determining the number and arrangement of electrodes included in the electrode array according to a structure of a target area to which an electrical stimulation is to be applied.

Specifically, a medical image of the target area where stimulation is to be applied is obtained. Here, the medical image includes at least one of CT, MRI, and an ultrasonic wave. Next, an image segmentation technique is applied to the acquired medical image to generate a three-dimensional tissue model, and a virtual electrode array is inserted into the generated three-dimensional tissue model.

Next, a simulation is performed such that the strength of an induced electric field in the target area reaches a preset threshold during electrical stimulation by applying stimulation to the three-dimensional tissue model through the inserted virtual electrode array.

By using repetitive simulation results, a combination using the smallest number of electrodes that satisfies an electric field critical condition is derived, and the electrode array is optimized by determining arrangement of electrodes by using the derived combination of the electrodes.

Here, the electrodes may be arranged in only an area corresponding to the target area in consideration of a structure of the target area and the number of electrodes. For example, when the target area is hippocampus, multiple microelectrodes may be arranged in a longitudinal direction of the hippocampus by considering narrow and long structural characteristics. Since a structure and size of the target area may differ for each area, personalized electrical stimulation treatment may be performed by determining the number and arrangement of electrodes included in the electrode array through simulation according to the information on the target area obtained by analyzing a medical image of a target person.

In step S120 of setting a stimulation parameter, sequential stimulation parameters including stimulation intensity, a stimulation sequence, and a stimulation pulse may be determined based on the structure of the target area for the optimized electrode array.

Specifically, the stimulation intensity may be determined such that electric field stimulation of intensity greater than or equal to a first threshold is applied to an area of a preset ratio (for example, 50%) or more of the total volume of the target area and electric field stimulation with average intensity less than a second threshold is applied to areas (that is, areas within a certain distance affected by stimulation and around the target area) excluding the target area. Here, the first threshold is set to a preset electric field strength according to the target area and/or stimulation purpose, and the second threshold may be set to an electric field strength of a preset ratio (for example, 20%) of the first threshold.

For example, when applying stimulation to the hippocampus to suppress epileptic seizure, the first threshold may be set to 100 mV/mm which is an electric field strength known to be required to suppress epileptic seizures, and the second threshold may be set to 100 mV/mm, and the second threshold may be set to 200 mV/mm which is an average of an electric field strength within 1 mm around the hippocampus.

Also, when stimulation is applied to neurons to activate the neurons, the first threshold may be set to 10 to 50 mV/mm which is the electric field strength known to be required to activate neurons. For example, the first threshold of spinal nerve stimulation may be set to 50 mV/mm and the second threshold of spinal nerve stimulation may be set to 10 mV/mm which is an average of the electric field strength formed within 2 mm around the target area.

Also, the stimulation sequence may be set such that the stimulation is applied sequentially in one direction according to the arrangement of electrodes from an electrode located at one end of the electrode array to an electrode located at the other end. Meanwhile, the unidirectional direction may be forward or reverse, but it is preferable that the applied stimulation proceeds sequentially.

Also, a width of a stimulation pulse and an interval between pulses may be set in a range where stimulation energies sequentially applied by the stimulation pulse overlap each other.

In addition, it is preferable that the interval between stimulation pulses does not exceed an active potential time.

The width of the stimulation pulse is determined by considering the strength of an induced electric field within a predefined target area so as to satisfy a strength-duration curve depending on purposes of stimulation.

Finally, a stimulation frequency may be set variously to low and high frequencies depending on purposes of stimulation. However, a stimulation cycle corresponds to the reciprocal of a frequency (1/frequency), and is preferably set to be less than or equal to the sum of a width of the stimulation pulse and an interval between pulses.

In step S310 of applying sequential stimulation, sequential stimulation may be applied to the target area through the electrode array by using the determined sequential stimulation parameter.

In the sequential local electrical stimulation method described above with reference to FIG. 1, optimization of an electrode array and setting of a stimulation parameter may be performed by a simulation device capable of simulating electrical stimulation based on an input medical image and an anatomical structure of a target person.

Figure 2:
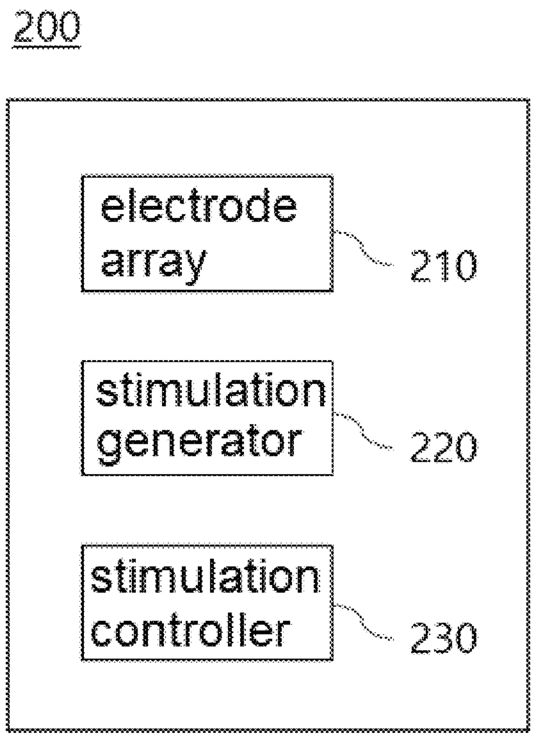
FIG. 2 is a configuration diagram of a sequential local electrical stimulation device according to an embodiment of the present disclosure.

FIG. 2 is a configuration diagram of a sequential local electrical stimulation device according to an embodiment of the present disclosure.

As illustrated in FIG. 2, a sequential local electrical stimulation device 200 may include an electrode array 210, a stimulation generator 220, and a stimulation controller 230.

The electrode array 210 includes multiple electrodes, and the number and arrangement of electrodes included in the electrode array 210 are determined according to a structure of a target area.

The stimulation generator 220 generates electrical stimulation under control by the stimulation controller 230 and applies the electrical stimulation to a target area through the electrode array 210.

The stimulation controller 230 determines sequential stimulation parameters including stimulation intensity, a stimulation sequence, and a stimulation interval based on a structure of the target area for the electrode array 210, and control stimulation generator 220 according to the determined sequential stimulation parameters.

In the following description, a sequential local electrical stimulation method according to an embodiment of the present disclosure and effects thereof are described in detail with reference to FIGS. 3A to 7H and a specific experimental example in which the hippocampus is set as the target area to suppress epileptic seizure. However, the present disclosure is not limited thereto and may be applied to various stimulation sites.

An array of four pairs of electrodes is selected which relatively reduces tissue damage caused by electrode insertion, reduces a surrounding electric field capable of inducing unintended neural responses with relatively low stimulation intensity, and induces an electric field sufficient to inhibit an epileptic network.

Next, the smallest value indicating an antiseizure effect for each target through appropriate intensity of the stimulation amplitude in a step of 50 μA (maximum 650 and 140 μA respectively for sequential narrow-field (SNF) stimulation and low-intensity wide-field (LIWF) stimulation) is set as a threshold.

Next, seizure is identified by using a criterion that the power spectral density of a specific band (alpha, beta, and gamma bands) during 5 minutes after seizure induction is more than twice a baseline. In this case, when any one of channel thresholds is satisfied, a stimulation trigger signal is generated.

In addition, spike characteristics including an amplitude, a speed, and regularity, are calculated by performing fine tuning for each person to be used to determine a trigger output, and in order to prevent a false alarm, certain repetitive characteristics caused by an abnormal pattern and an external artifact, such as an abnormally large amplitude signal, are excluded from a detection process.

In addition, in unilateral WF, bilateral WF, bilateral LIWF, unilateral SNF, and bilateral SNF stimulation groups, a stimulation module transmits an electrical pulse to the hippocampal area when receiving a trigger signal from a customized seizure detector. In order to continuously apply stimulation until the seizure terminates and to prevent excessive stimulation, a non-stimulation interval of 10 seconds is set for each stimulation.

Figure 3A:
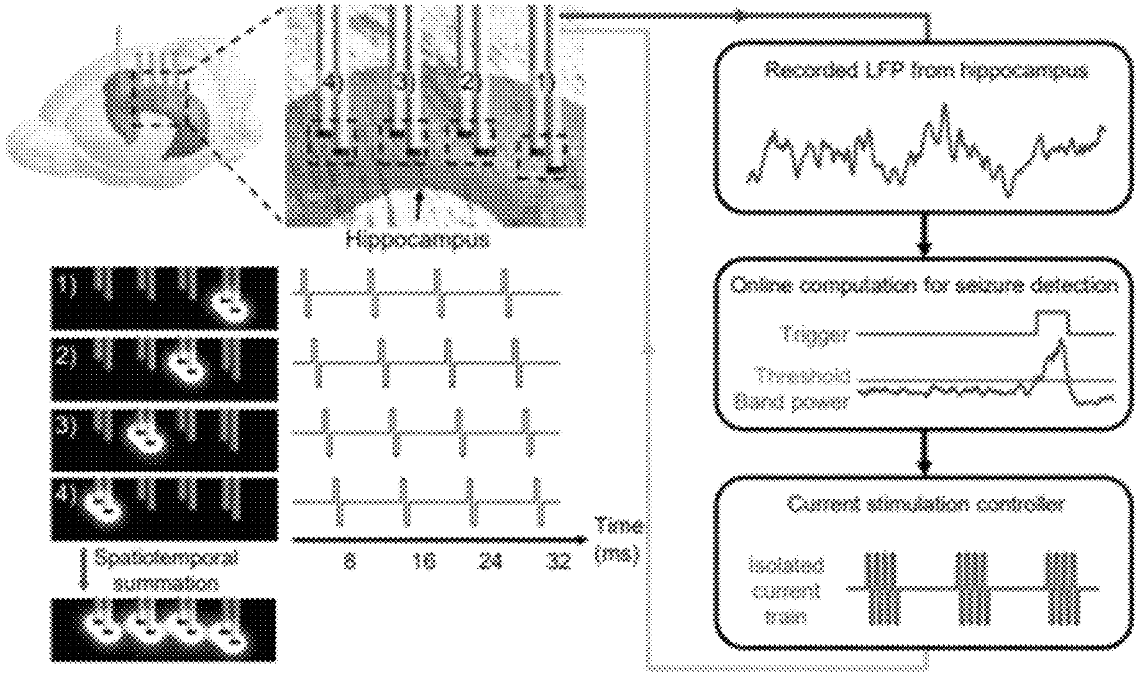
FIGS. 3A and 3B illustrate a conceptual overview of an on-demand sequential narrow-field (SNF) pulse stimulation method and an operating principle thereof.
Figure 3B:
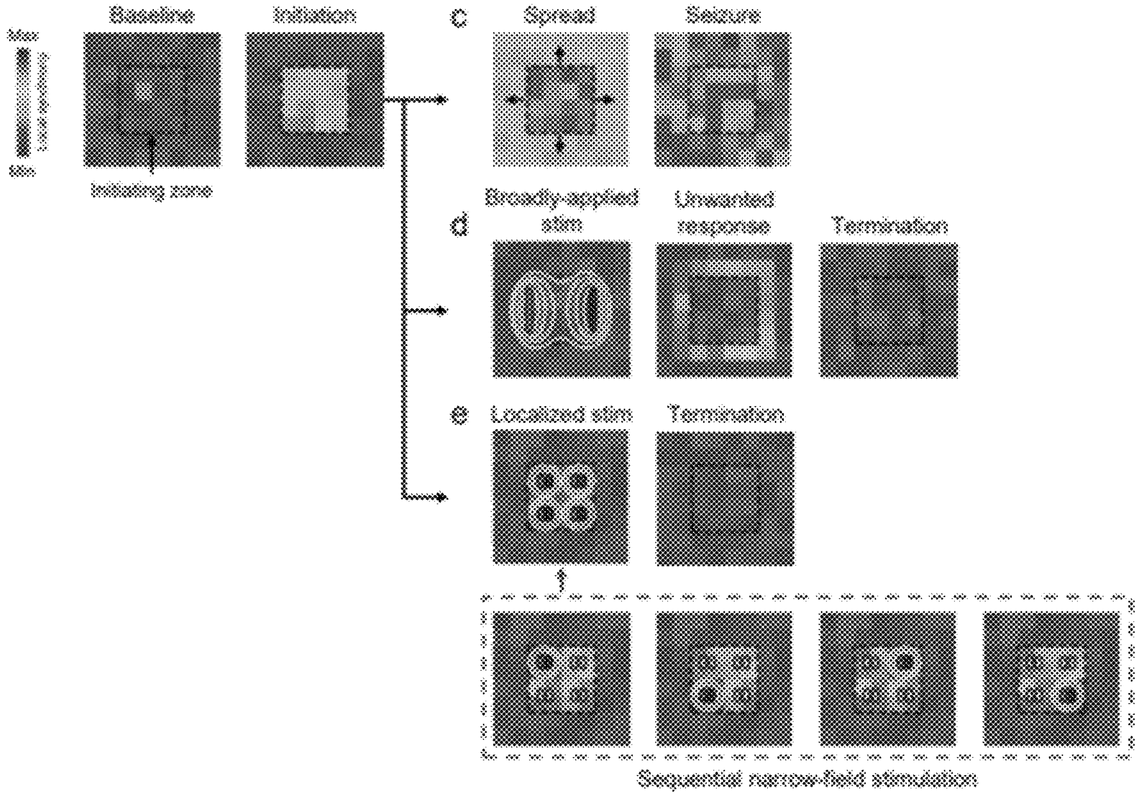
Figure 4A:
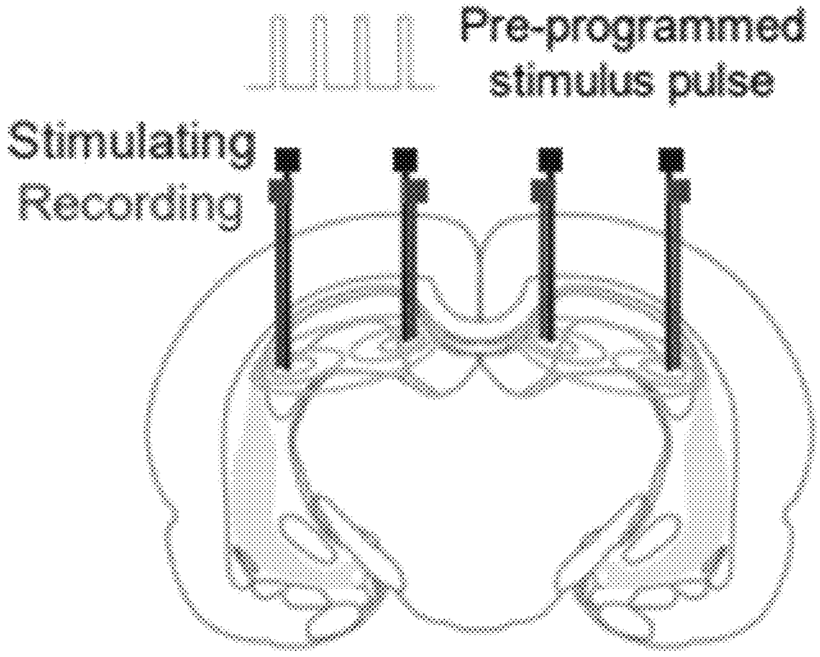
FIGS. 4A to 4H illustrate a method of controlling seizure of a KA-induced SE model through overall hippocampal intervention.
Figure 4B:
Figure 4C:
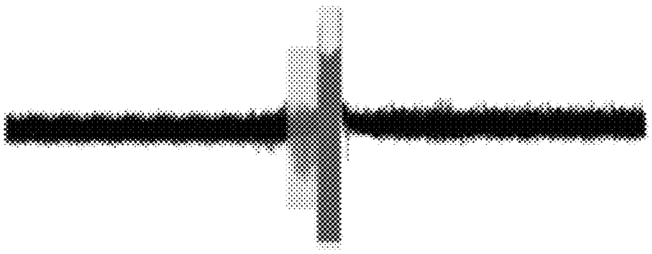
Figure 4D:
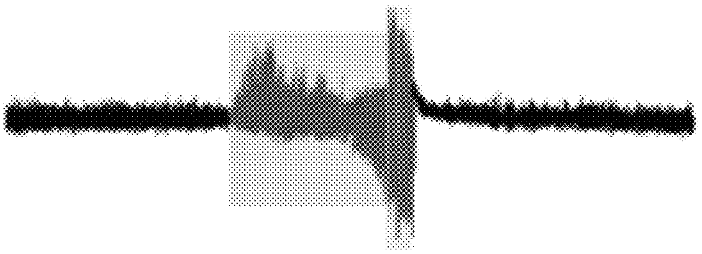
Figure 4E:
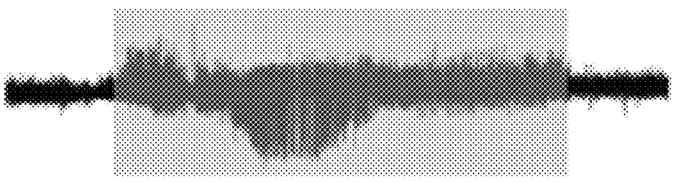
Figure 4F:
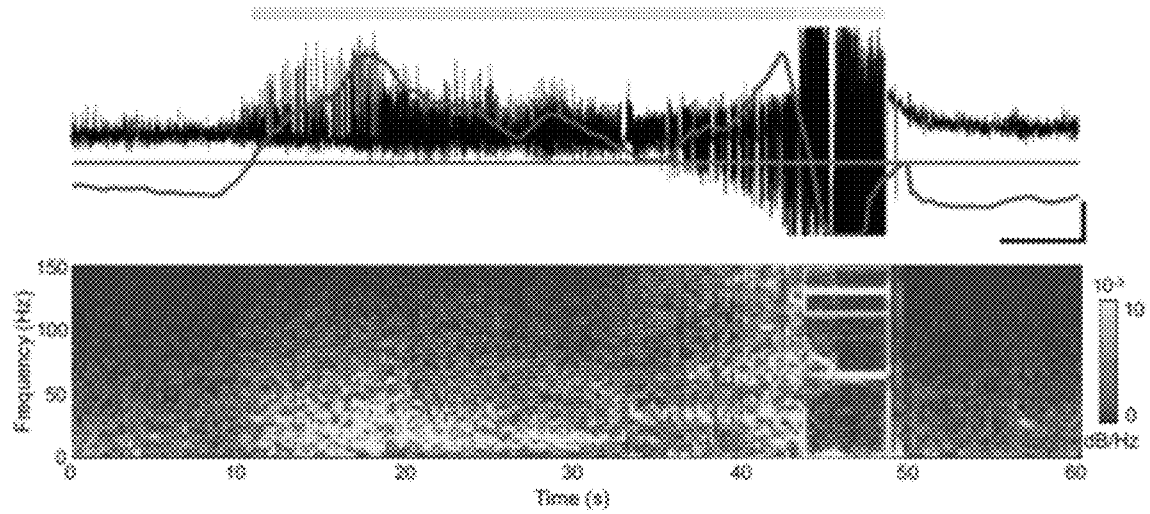
Figure 4G:
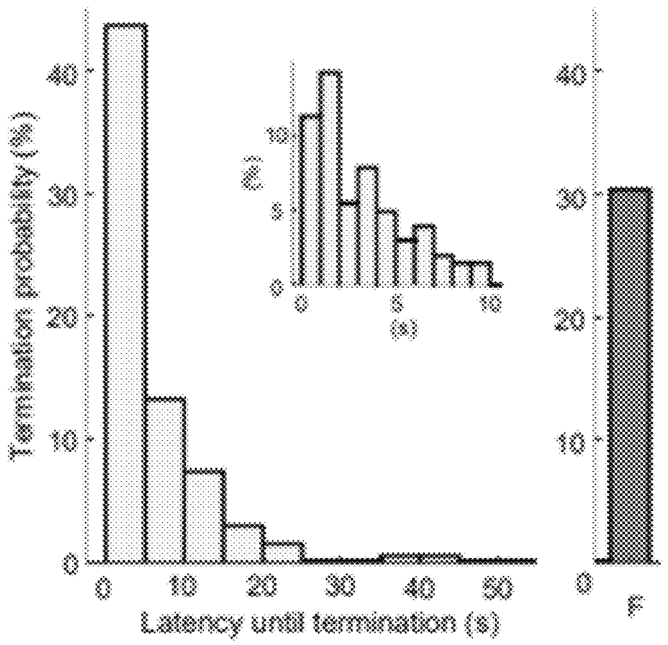
Figure 4H:
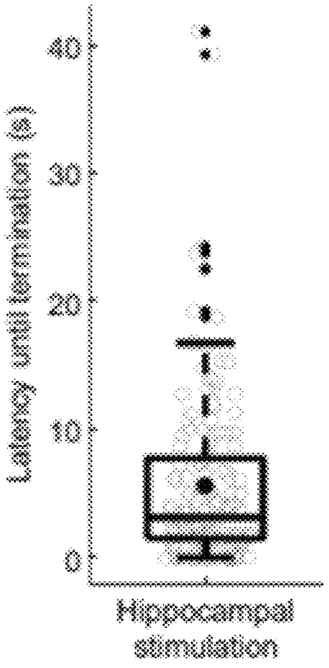

FIGS. 3A and 3B illustrate a conceptual overview of an on-demand sequential narrow-field (SNF) pulse stimulation method and an operating principle thereof.

As illustrated in FIGS. 3A and 3B, depth electrodes inserted into bilateral hippocampal areas are used to record a local field potential (LFP) and stimulate the entire hippocampal structure. LFPs recorded from the left and right hippocampi are used to identify abnormal brain activity in real time, and when electromagnetic seizure is detected based on power of a specific band of the LFPs, a short stimulation pulse is applied to an electrode array. As a result, multiple local electric fields are sequentially induced to intervene in seizure activity.

As illustrated in FIG. 3B, a diagram including a matrix indicating a level of neural synchronization conceptually illustrates a more detailed treatment mechanism and a benefit of the stimulation method according to the present disclosure. when an initial electromagnetic seizure activity of temporal lobe epilepsy (TLE) appears in a limited area without timely intervention, an electromagnetic seizure activity may progress to another brain area. In this case, when epileptic seizure is detected at an early stage by appropriate control of a specific area related to pathological synchronization, a seizure activity may terminate, and accordingly, hippocampal stimulation may be an appropriate treatment strategy of TLE. However, stimulation applied broadly at once to fully adjust a large hippocampal structure may induce a fringing field that spreads outside a target tissue, causing unintended stimulation outside the target area. Therefore, the stimulation method according to the present disclosure may effectively control the entire area of the hippocampus to terminate seizure with multiple sequentially induced local fields, thereby avoiding a fringing field effect that may cause unwanted excessive stimulation-related response outside a target area.

FIGS. 4A to 4H illustrate a seizure control method of a KA-induced SE model through overall hippocampal intervention.

As illustrated in FIGS. 4A to 4H, in order to demonstrate the therapeutic efficacy of the stimulation method according to the present disclosure, a therapeutical possibility of the entire hippocampal modulation in TLE is first evaluated by using previously programmed stimulus that repeatedly intervenes the hippocampal network at a fixed rate.

A depth electrode is implanted in a hippocampal space to control the entire hippocampal area and monitor brain activity. Next, intraperitoneal kainic acid (KA) is injected to reproduce neuropathological and electroencephalographic characteristics of a TLE patient. As a result, it may be seen that electro-recording seizure is quickly suppressed by stimulation compared to unstimulated seizure.

FIGS. 5A to 5G illustrate effects of closed-loop unilateral and bidirectional control of temporal lobe seizure.

In addition, epileptic seizure of a TLE patient may occur in the unilateral or bilateral hippocampus, and similarly, seizure activity of the KA-induced SE model may initiate unilaterally or bilaterally in a hippocampal area. Therefore, numerous studies on unilateral (including ipsilateral and contralateral approaches) and bilateral deep brain stimulation (DBS) regarding an affected area have been performed as part of preclinical trials and patient trials. Additionally, bilateral hippocampal adjustment has been reported to have superior efficacy in terms of suppression of seizure even in unilateral TLE. However, careful evaluation of the therapeutic effect of the entire hippocampal stimulation in bilateral configurations has rarely been investigated compared to a unilateral configuration.

Therefore, test was performed to check whether WF stimulation applied unilaterally or bilaterally to formation of the entire hippocampus at the right time induces another synchronization of a neuronal network during seizure and results in difference in inhibitory efficacy. To this end, a closed-loop seizure control system was implemented in both unilateral and bilateral configurations, and a phase synchronization index between two hemispheres was investigated.

Figure 5A:
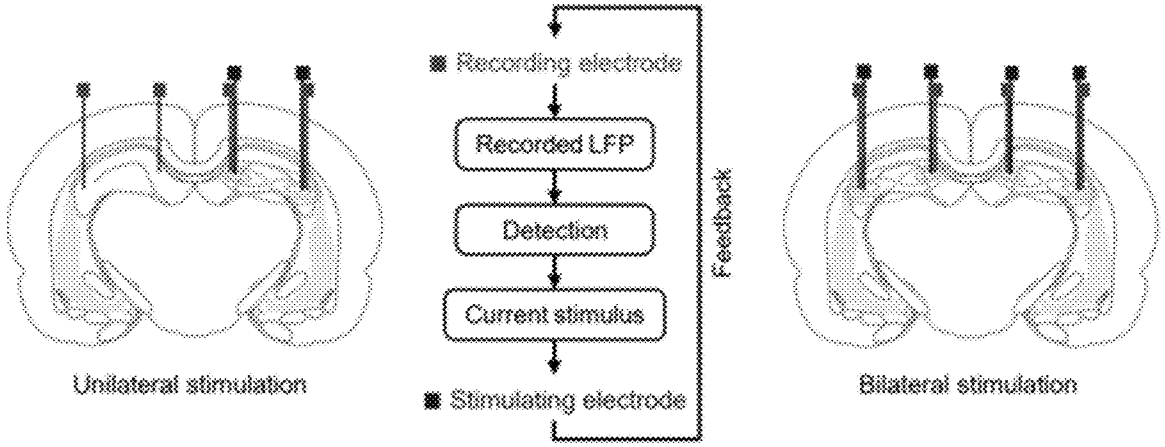
FIGS. 5A to 5G illustrate effects of closed-loop unilateral and bidirectional control of temporal lobe seizure.
Figure 5B:
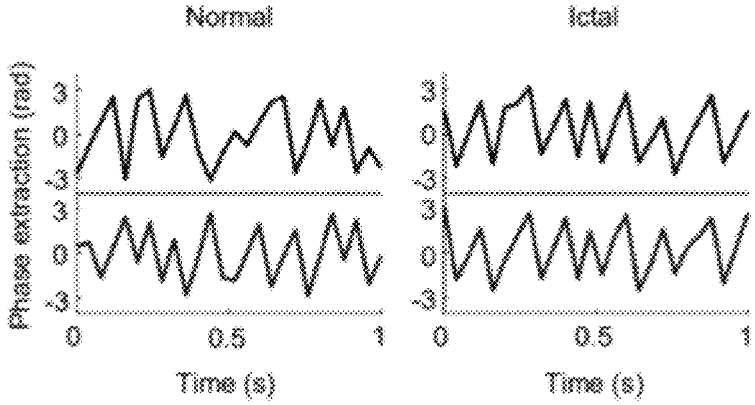
Figure 5C:
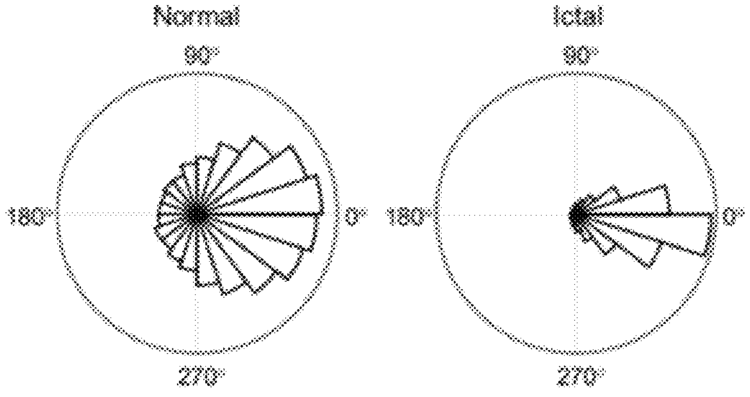
Figure 5D:
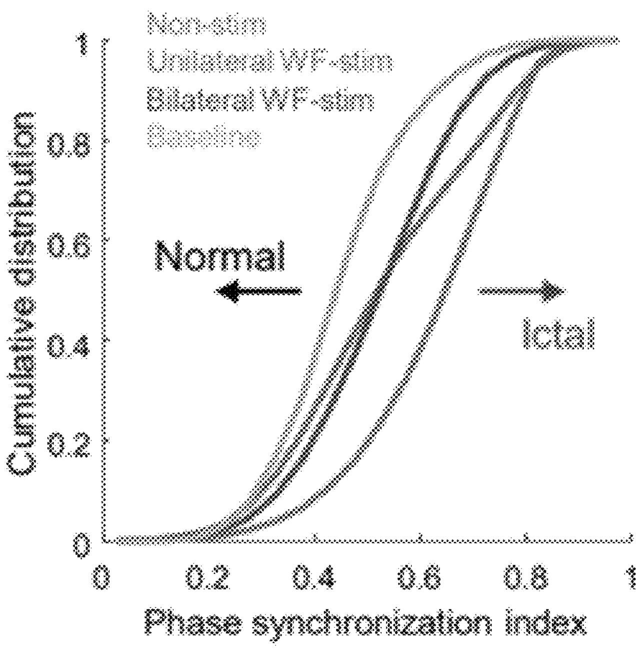
Figure 5E:
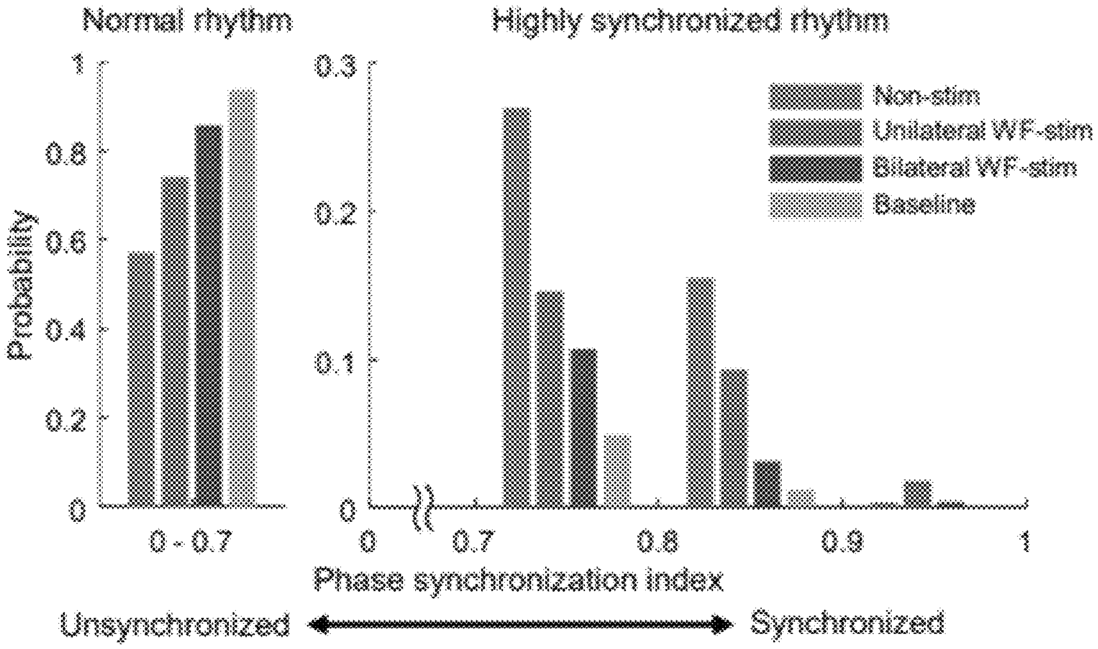
Figure 5F:
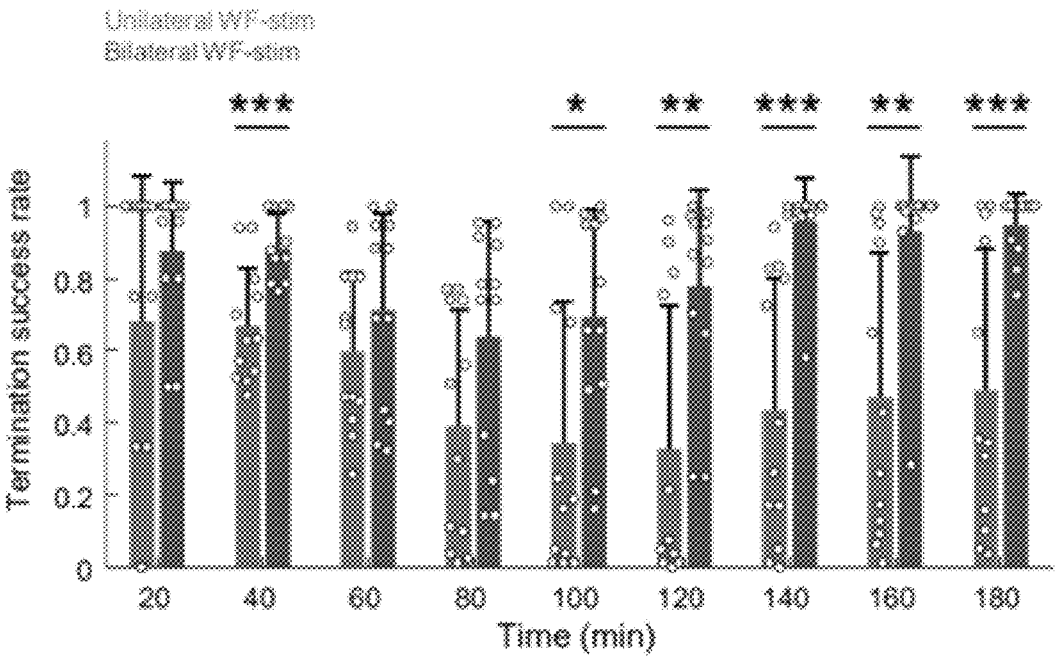

A phase of an extracted signal is illustrated in FIG. 5B. During seizure, phases of two hemispheres are very similar, and a phase difference is 0 degrees. A phase synchronization index during stimulation was investigated by using the phase difference between two hemispheres. A synchrony index of a baseline is skewed to the left (where low values are dominant) as illustrated in FIG. 5D, whereas a synchronization index of an unstimulated group is skewed to the right (where high values are dominant). Results from the unilateral and bilateral WF stimulation groups are between a baseline distribution and an unstimulated group and show a significant difference in phase synchronization around an exponent of 0.7, which is reported as a seizure value. The synchronization index of the baseline has the highest proportion in a normal range, and indicates a high proportion of stable brain activity in normal rhythm followed by a bilateral stimulation group, a unilateral stimulation group, and no stimulation group. The bilateral WF stimulation significantly suppresses hyper-synchronized neural rhythms compared to the unilateral configuration. A success rate of seizure termination according to unilateral and bilateral control was analyzed every 20 minutes, and a significant difference therebetween was found.

Figure 5G:
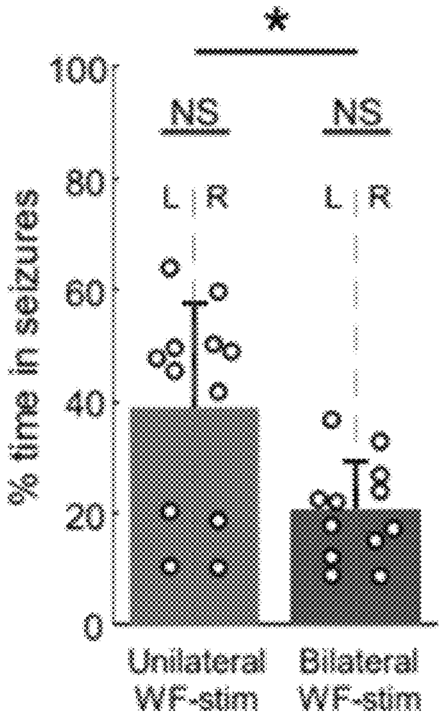

As a result, a total seizure duration of bilateral stimulation was 18.6% (FIG. 5G; 20.3% and 38.9% respectively for bilateral and unilateral WF stimulation; Mann-Whitney U test; P=0.0226 for comparison between two conditions; P=0.9362 for all in-group comparisons between left and right hemispheres) and is shorter than a total seizure duration of unilateral stimulation, and there was a significant decrease in band power during bilateral WF stimulation compared to the unilateral stimulation. In conclusion, the finding indicates that bilateral hippocampal stimulation may effectively desynchronize a neural network during a seizure period compared to a unilateral configuration, resulting in a significant difference in seizure suppression effect.

The therapeutic efficacy of entire hippocampal stimulation of TLE is demonstrated by the closed-loop WF stimulation. However, as described above, WF stimulation may induce unintended neural response due to a fringing field effect that may result in unwanted gradient distributions in an area adjacent to a target area.

Therefore, in the experimental example of the present disclosure, intracerebral electric fields induced by WF and SNF stimulation were measured and a difference in the electric field induced outside a hippocampal structure was quantitatively compared.

FIGS. 6A to 6L illustrate results of comparing fringing field effects during in vivo and in silico stimulation.

As illustrated in FIGS. 6A to 6L, depth electrode arrays for generating stimulation and recording induced potentials was first implanted in the hippocampus and the entire brain. In this case, a stimulation current was applied individually to each of five electrode configurations, and intracerebral potentials were recorded to calculate an induced voltage gradient. An electric field distribution due to a widely applied current spread much farther than the induced field due to a narrowly applied current.

In order to check a difference in activated volume due to stimulation pulses, a ratio of an area with off-target diffusion fields exceeding 10 mV/mm and 50 mV/mm was compared for WF and SNF conditions.

In both comparisons, results show significant differences between WF and SNF stimulation and clearly suggest superiority of SNF stimulation in preventing unwanted activation or inhibition of off-target tissues compared to the WF stimulation. Linear diffusion properties were further investigated in consideration of a direction of a main field vector, and results thereof show that there were significant differences between the WF and SNF conditions as examined two-dimensionally in the entire brain.

Figure 6A:
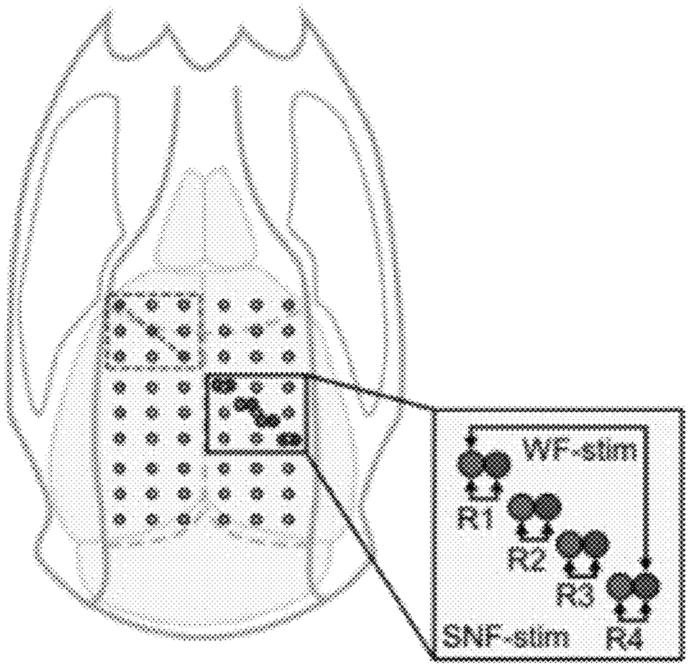
FIGS. 6A to 6L illustrate results of comparing fringing field effects in vivo and during silico stimulation.
Figure 6B:
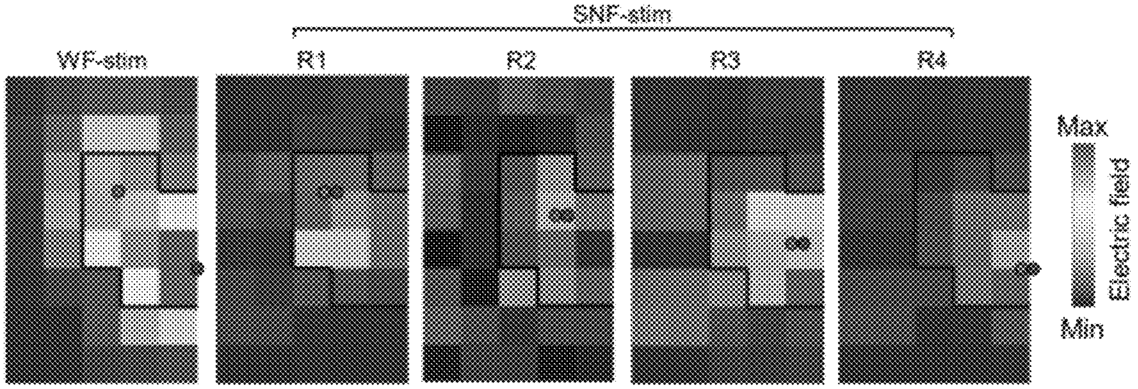
Figure 6C:
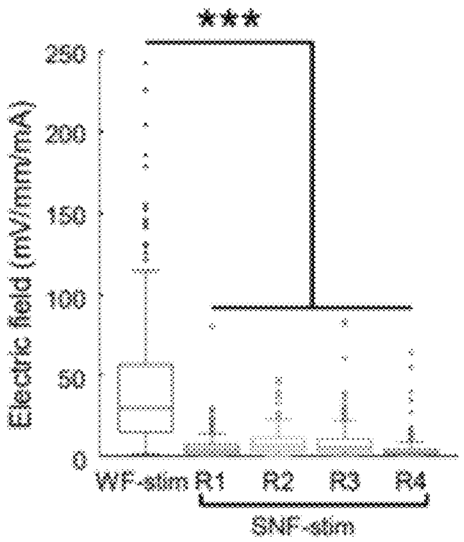
Figure 6D:
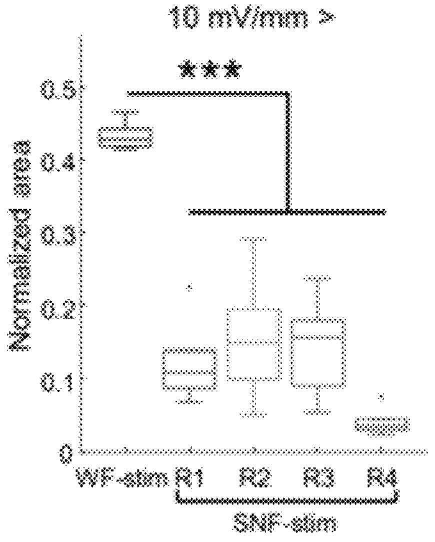
Figure 6E:
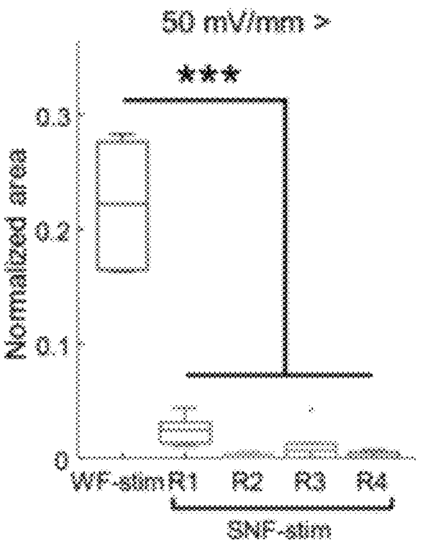
Figure 6F:
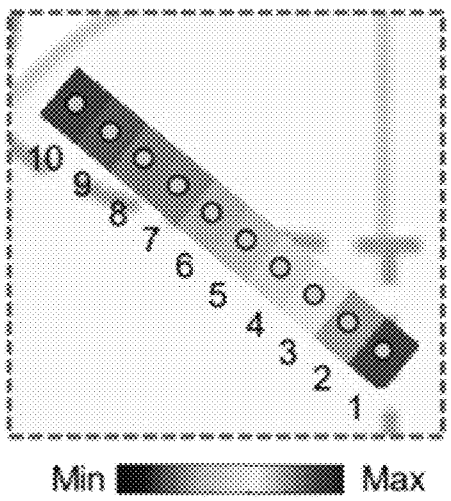
Figure 6G:
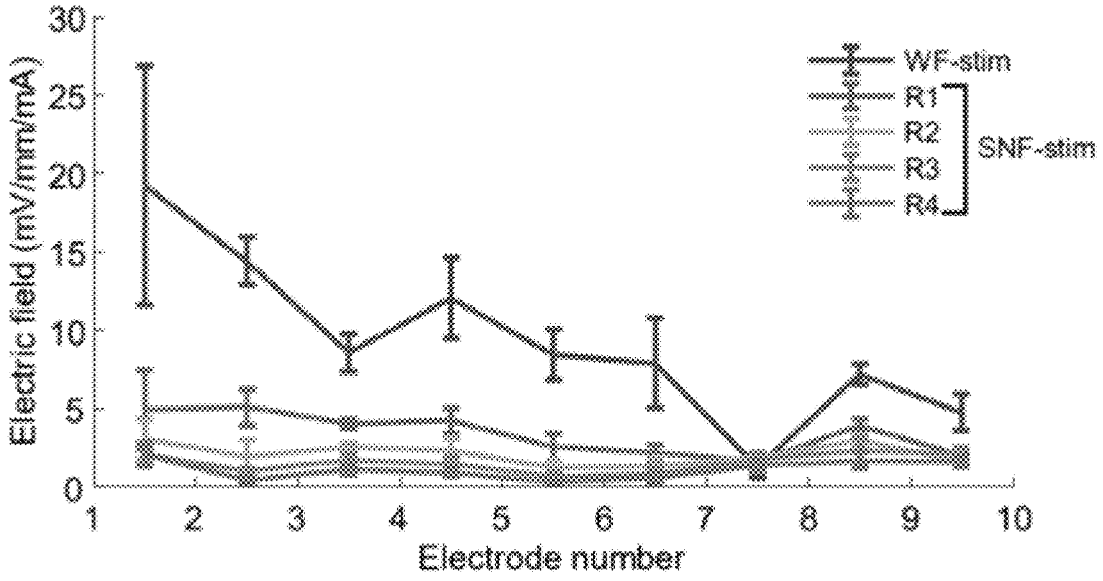
Figure 6H:
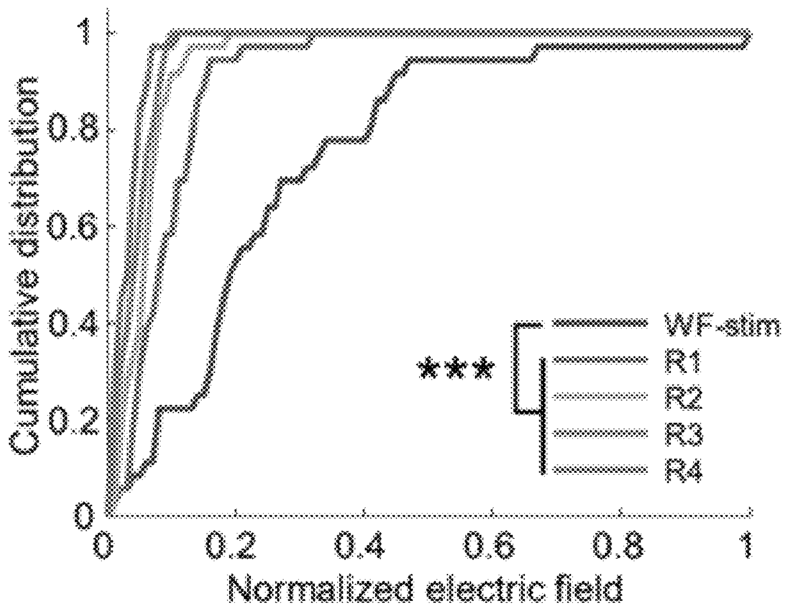
Figure 6I:
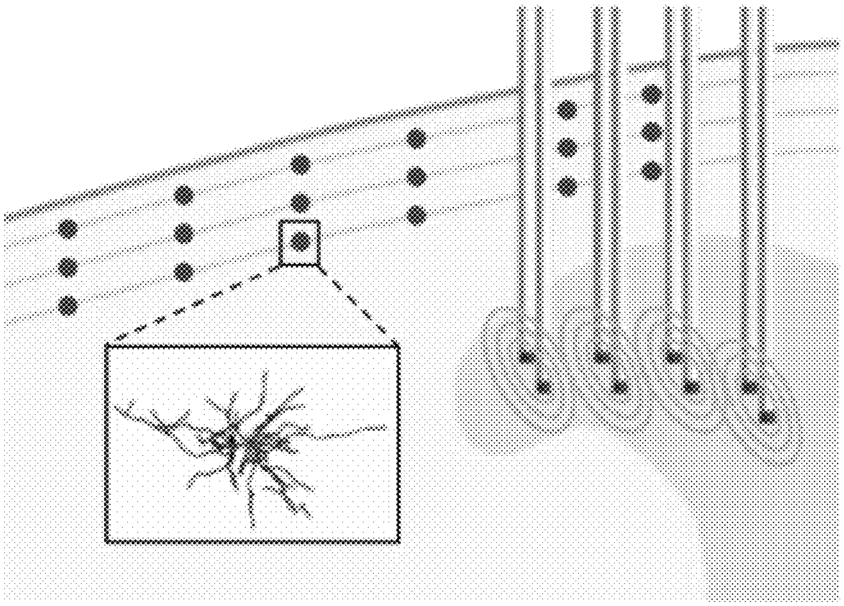
Figure 6J:
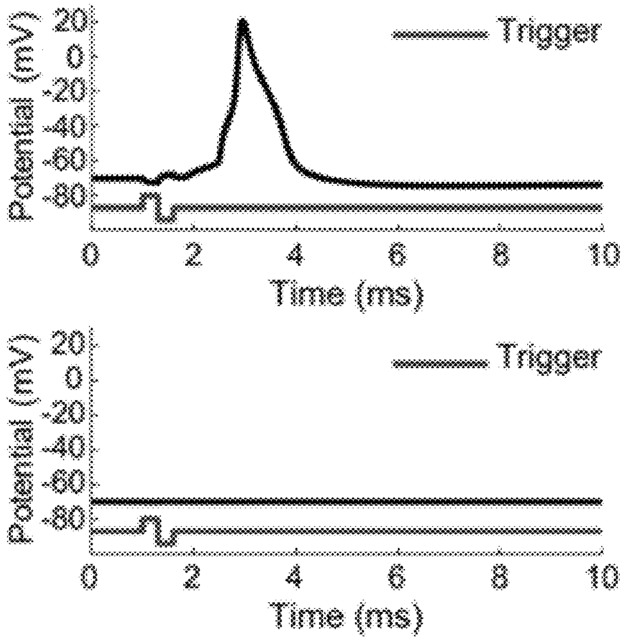
Figure 6K:
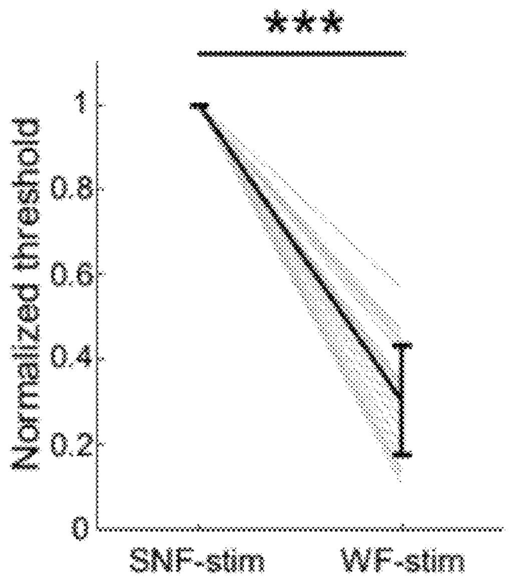

Because neuronal membranes may transiently integrate multiple fields in similar vector directions due to inherent properties thereof, it is not easy to conclude that SNF stimulation does not induce unwanted stimulation compared to WF stimulation. Therefore, neural responses of a primary motor cortex M1 induced by SNF and WF stimulation methods were compared to each other by using a computational model that may reproduce neural properties by integrating multiple electrical gradients applied in a short time (FIG. 61 and FIG. 6J). As a result, normalized thresholds for the neural responses of M1 due to SNF hippocampal stimulation were significantly greater than WF stimulation, ranging from 2 to 9 times for each position (FIG. 6K, 1.00 and 0.30 respectively for SNF stimulation and WF stimulation, paired t-test, P<0.001, n=18 recording points for each group).

Figure 6L:
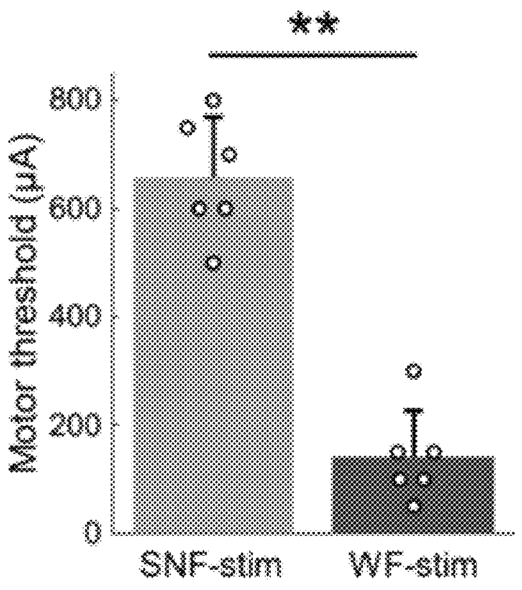
Figure 7A:
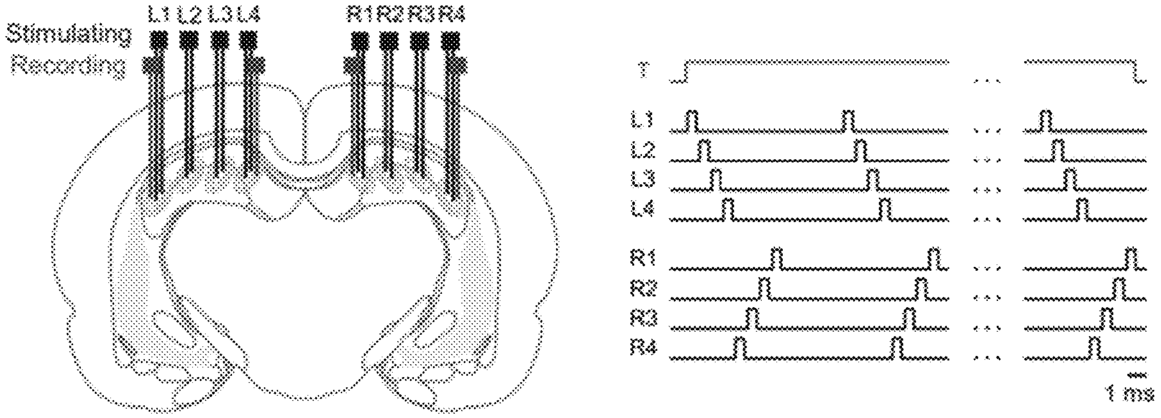
FIGS. 7A to 7H illustrate results of comprehensive analysis of SNF stimulation for suppression of seizure.
Figure 7B:
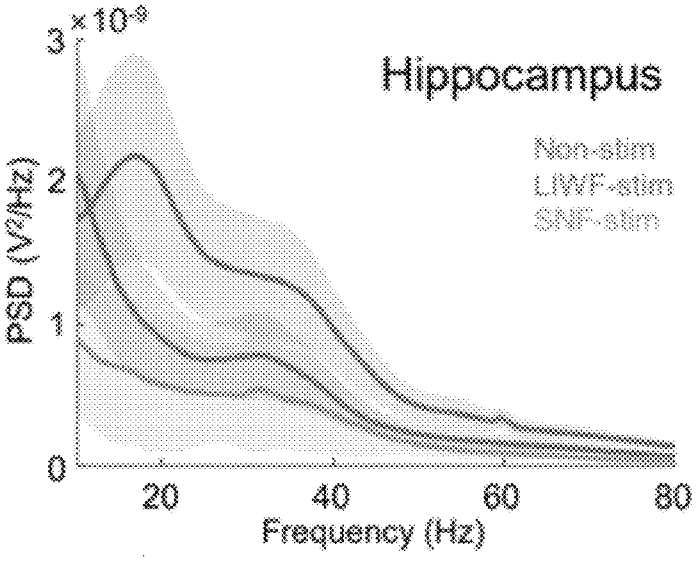
Figure 7C:
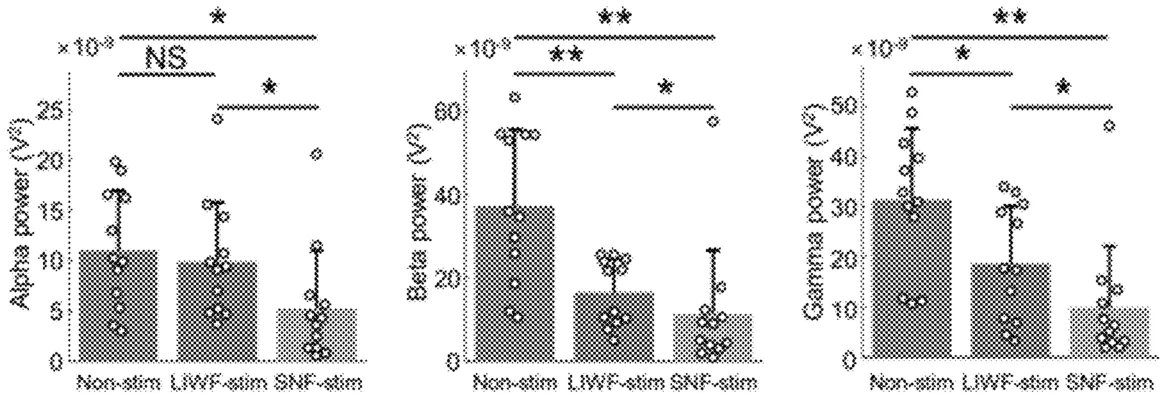
Figure 7D:
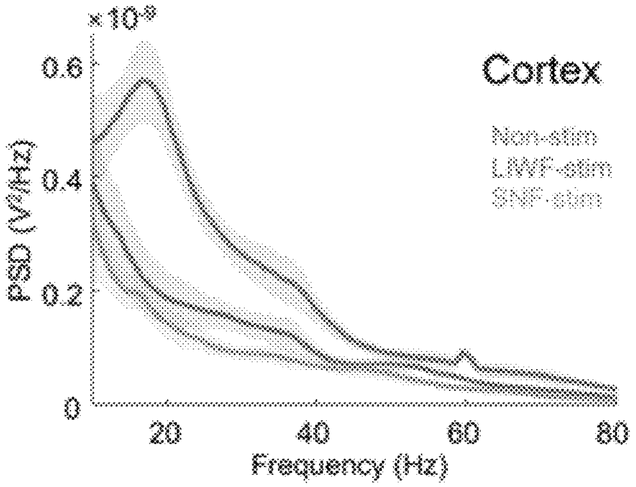
Figure 7E:
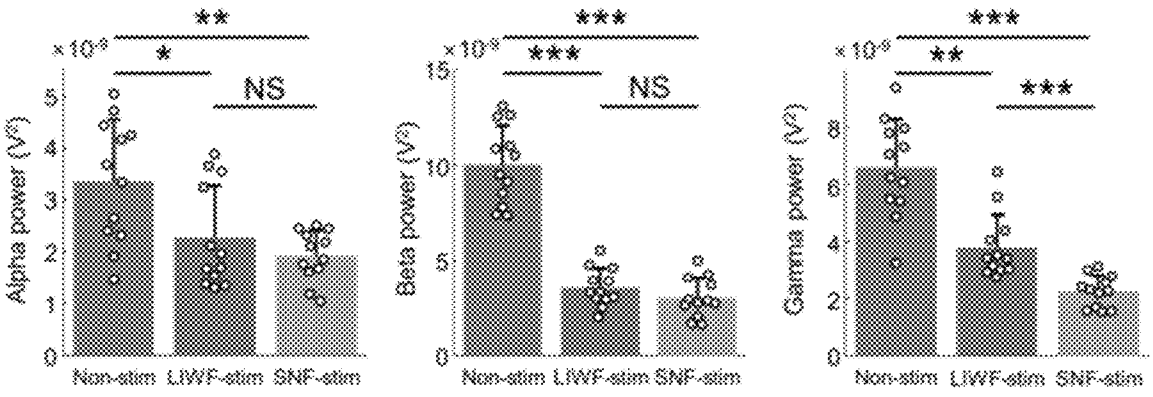
Figure 7F:
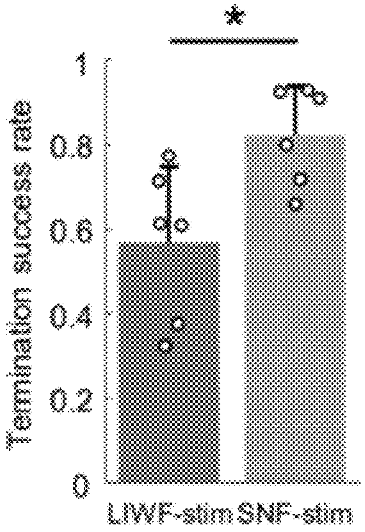
Figure 7G:
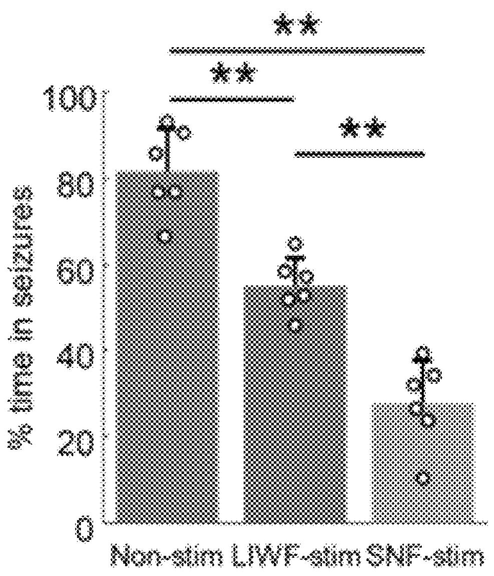
Figure 7H:
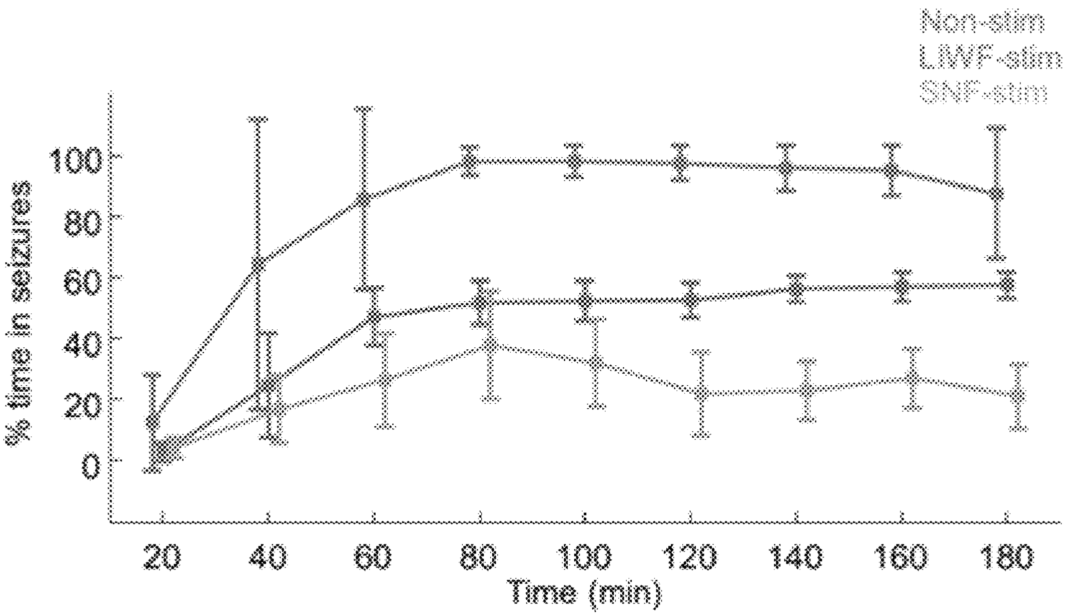

Similarly to the numerical simulation results, SNF stimulation requires a stimulation current greater approximately 4.6 times than WF stimulation to induce an abnormal motion response (FIG. 6L: 658 μA and 142 μA respectively for SNF stimulation and WF stimulation, Mann-Whitney U test, P=0.0048, n=6 animals for each group). Here, in order to fairly compare anticonvulsant effects during stimulation within a range of acceptable clinical translation by using in vivo and in silico results, a safety threshold of stimulation intensity representing a maximum current level that does not induce abnormal motion and sensory responses was set (650 μA and 140 μA respectively for SNF stimulation and WF stimulation). Then, a brain electrophysiological activity was comprehensively analyzed during acute SE for a non-stimulation group, a WF stimulation group, and an SNF stimulation group within the safety threshold, and WF stimulation of a safe level was set to LIWF stimulation.

FIGS. 7A to 7H illustrate comprehensive analysis results of SNF stimulation for suppression of seizure.

Custom electrode arrays for SNF stimulation are implanted into both sides of the hippocampus in a similar manner to the electrode configuration of WF stimulation. The power of alpha (8-13 Hz), beta (13-30 Hz) and gamma (30-80 Hz) frequency activity is significantly reduced during LIWF and SNF stimulation compared to non-stimulation, except alpha power for a LIWF condition. Also, the SNF stimulation suppresses epileptic rhythm more than the LIWF stimulation, and thereby, the proposed SNF stimulation may significantly suppress excessive neural rhythm at a safe level in both the hippocampus and cortex compared to the LIWF stimulation (FIG. 7C and FIG. 7E, Kruskal-Wallis test, P=0.019, <0.001 and 0.0016 respectively for alpha, beta and gamma power in hippocampus, P=0.01 for alpha in cortex and P<0.01 for alpha and beta and gamma power comparison, n=12, six animals for each group). Accordingly, success rates of seizure termination using the LIWF and SNF stimulation types are significantly different from each other (FIG. 7F, 0.57 and 0.82 respectively for LIWF and SNF stimulation, Mann-Whitney U test, P=0.0202, n=6 animals for each group). Likewise, a total seizure duration is significantly reduced by the SNF stimulation compared to the LIWF-stimulated and unstimulated groups (FIG. 7G; 81.5%, 55.1%, and 27.7% respectively for the unstimulated group, LIWF-stimulated group, and SNF-stimulated group, Kruskal-Wallis test, P<0.001, 2(2)=15.16, n=6 animals for each group). Also, seizure periods during LIWF and SNF stimulation are divided at intervals of 20 minutes and further analyzed, which reveal significantly different trends during most periods.

As a result of investigating seizure suppression effects including early termination of hippocampal seizure and termination of fully disseminated seizure by further analyzing the experimental data of unstimulated and SNF-stimulated groups, the SNF stimulation was found to suppress epileptic rhythm under diffusion condition as well as hippocampal onset. Also, by investigating an antiseizure effect during unilateral versus bilateral SNF stimulation, it was confirmed that the bilateral configuration had superior effects on spectral density, phase synchronization, and seizure duration during control. Overall, by combining in vivo and in silico experiments with each other, it was proved that SNF stimulation may effectively adjust a hippocampal area and suppress epileptic seizure while preventing unwanted stimulation.

In this way, according to the present disclosure, by placing an electrode array including multiple electrodes in an area corresponding to a target area according to a structure of the target area and sequentially applying local electrical stimulation to the multiple electrodes, symptoms may be effectively improved in a short period of time while minimizing an impact on surrounding areas of the target area.

The present disclosure is described with reference to the embodiments illustrated in the drawings, and the embodiments are merely illustrative, and those skilled in the art in which the present disclosure belongs will understand that various modifications and other equivalent embodiments may be derived therefrom. Therefore, the true technical protection scope of the present disclosure should be determined by the technical idea of the patent claims below.

What is claimed is:

1. A sequential local electrical stimulation device comprising:

an electrode array including multiple electrodes, wherein a number and arrangement of the multiple electrodes are determined according to a structure of a target area;

a stimulation generator configured to apply electrical stimulation to the target area through the electrode array; and a stimulation controller configured to:

determine stimulation parameters including stimulation intensity, a stimulation sequence, and a stimulation interval based on the structure of the target area by deriving a combination using a smallest number of electrodes that satisfies an electric field critical condition through repetitive simulation results, wherein the stimulation sequence applies stimulation sequentially from a distal electrode to a proximal electrode along the electrode array; and control the stimulation generator according to the determined stimulation parameters.

2. The sequential local electrical stimulation device of claim 1, wherein the target area comprises a hippocampus, and wherein the multiple electrodes comprise microelectrodes arranged along a longitudinal direction of the hippocampus.

3. The sequential local electrical stimulation device of claim 1, wherein the electrode array comprises four pairs of electrodes.

4. The sequential local electrical stimulation device of claim 1, wherein the stimulation controller is configured to apply stimulation bilaterally to sides of the target area.

5. The sequential local electrical stimulation device of claim 1, further comprising a seizure detector configured to generate a trigger signal for the stimulation controller.

6. The sequential local electrical stimulation device of claim 1, wherein the stimulation parameters further include a stimulation frequency and a stimulation cycle.

7. The sequential local electrical stimulation device of claim 6, wherein the stimulation frequency is set according to a stimulation purpose.

8. The sequential local electrical stimulation device of claim 7, wherein the stimulation cycle is set to be less than or equal to a sum of a width of a stimulation pulse and an interval between pulses.

9. A sequential local electrical stimulation method using a sequential local electrical stimulation device, the sequential local electrical stimulation method comprising:

determining a number and arrangement of electrodes included in an electrode array according to a structure of a target area;

determining stimulation parameters including stimulation intensity, a stimulation sequence, and a stimulation pulse based on the structure of the target area by deriving a combination using a smallest number of electrodes that satisfies an electric field critical condition through repetitive simulation results; and sequentially applying stimulation in one direction from an outermost part of the electrode array according to the stimulation parameters.

10. The sequential local electrical stimulation method of claim 9, wherein the determining of the number and arrangement of the electrodes includes:

acquiring a medical image of the target area;

generating a three-dimensional tissue model by applying an image segmentation technique to the medical image and inserting a virtual electrode array into the three-dimensional tissue model; and performing a simulation such that intensity of an induced electric field in the target area reaches a preset threshold during electrical stimulation by applying stimulation through the virtual electrode array.

11. The sequential local electrical stimulation method of claim 9, wherein, in the determining of the stimulation parameters, the stimulation intensity is determined such that electric field stimulus with an intensity greater than or equal to a first threshold is applied to the target area greater than or equal to a preset ratio of a total volume of the target area and electric field stimulation with an average intensity less than a second threshold is applied to an area within a preset distance from an area excluding the target area, wherein the intensity of the electric field stimulus is calculated based on induced voltage gradients measured during generation of the repetitive simulation results using a three-dimensional tissue model, and wherein the stimulation intensity is adjusted during the simulations to achieve the first threshold and the second threshold.

12. The sequential local electrical stimulation method of claim 11, wherein the first threshold is set to an electric field strength according to at least one of the target area and a stimulation purpose, and the second threshold is set to an electric field strength of the preset ratio of the first threshold.

13. The sequential local electrical stimulation method of claim 12, wherein the stimulation purpose is treating epilepsy.

14. The sequential local electrical stimulation method of claim 9, wherein, in the determining of the stimulation parameters, the stimulation sequence is sequentially determined according to the arrangement of the electrodes from an electrode located at one end of the electrode array to an electrode located at an opposite end.

15. The sequential local electrical stimulation method of claim 9, wherein, in the determining of the stimulation parameters, a width of the stimulation pulse and an interval between pulses are determined in a range where stimulation energies applied by the stimulation pulse overlap each other.

16. The sequential local electrical stimulation method of claim 15, wherein the width of the stimulation pulse is determined by considering a strength of an induced electric field in a predefined target area to satisfy a strength-duration curve according to a stimulation purpose.

17. The sequential local electrical stimulation method of claim 9, wherein the repetitive simulation results are generated using a three-dimensional tissue model based on one or more medical images, the one or more medical images comprising at least one of a computed tomography (CT) image, a magnetic resonance imaging (MRI) image, and an ultrasonic wave image.

18. The sequential local electrical stimulation method of claim 9, further comprising detecting abnormal brain activity and, in response, generating a trigger signal to initiate the stimulation.

19. The sequential local electrical stimulation method of claim 18, wherein the detecting comprises recording local field potentials (LFPs) and identifying the abnormal brain activity based on power spectral density of a specific frequency band being more than twice a baseline.

* * * * *